US010765780B2

(12) United States Patent
Arimura et al.

(10) Patent No.: US 10,765,780 B2
(45) Date of Patent: Sep. 8, 2020

(54) METHOD OF PRODUCING TISSUE REGENERATION SUBSTRATE

(71) Applicant: GUNZE LIMITED, Ayabe-shi, Kyoto (JP)

(72) Inventors: Hidetoshi Arimura, Kyoto (JP); Keita Ide, Kyoto (JP)

(73) Assignee: GUNZE, LIMITED, Kyoto (JP)

( * ) Notice: Subject to any disclaimer, the term of this patent is extended or adjusted under 35 U.S.C. 154(b) by 406 days.

(21) Appl. No.: 15/524,922

(22) PCT Filed: Dec. 3, 2015

(86) PCT No.: PCT/JP2015/083968
§ 371 (c)(1),
(2) Date: May 5, 2017

(87) PCT Pub. No.: WO2016/088821
PCT Pub. Date: Jun. 9, 2016

(65) Prior Publication Data
US 2017/0312395 A1    Nov. 2, 2017

(30) Foreign Application Priority Data
Dec. 5, 2014    (JP) ................................ 2014-247083

(51) Int. Cl.
*B29C 65/62*    (2006.01)
*B32B 5/06*    (2006.01)
(Continued)

(52) U.S. Cl.
CPC ................ *A61L 27/56* (2013.01); *A61F 2/06* (2013.01); *A61F 2/105* (2013.01); *A61F 2/28* (2013.01);
(Continued)

(58) Field of Classification Search
CPC .......... B29C 65/62; B32B 5/022; B32B 5/06; B32B 5/26; B32B 2250/02;
(Continued)

(56) References Cited

U.S. PATENT DOCUMENTS

2004/0254640 A1    12/2004  Sutherland et al.
2011/0060413 A1*   3/2011   Kasuga ................. A61F 2/2846
                                                         623/16.11
(Continued)

FOREIGN PATENT DOCUMENTS

JP          5-076586        3/1993
JP        2004-148014       5/2004
(Continued)

OTHER PUBLICATIONS

Pham, et al., "Electrospun Poly(ε-caprolactone) Microfiber and Multilayer Nanofiber/Microfiber Scaffolds: Characterization of Scaffolds and Measurement of Cellular Infiltration", Biomacromolecules, 2006, 7 (10), pp. 2796-2805.

*Primary Examiner* — Leo B Tentoni
(74) *Attorney, Agent, or Firm* — Hamre, Schumann, Mueller & Larson, P.C.

(57) ABSTRACT

The present invention aims to provide a tissue regeneration substrate excellent in penetrability to cells as well as capable of effectively preventing cell leakage from the tissue regeneration substrate to accelerate tissue regeneration; and a method of producing the tissue regeneration substrate. The present invention relates to a tissue regeneration substrate including: a nonwoven fabric made of a bioabsorbable material, the tissue regeneration substrate having a laminated structure in which a layer containing a nonwoven fabric having an average pore size of 20 to 50 μm and a layer containing a nonwoven fabric having an average pore size of 5 to 20 μm are integrated.

4 Claims, 2 Drawing Sheets

(51) Int. Cl.
| | |
|---|---|
| *B32B 5/26* | (2006.01) |
| *D01D 5/08* | (2006.01) |
| *D02J 3/02* | (2006.01) |
| *D04H 3/105* | (2012.01) |
| *A61L 27/56* | (2006.01) |
| *A61L 27/34* | (2006.01) |
| *B32B 5/02* | (2006.01) |
| *D01D 5/098* | (2006.01) |
| *A61F 2/06* | (2013.01) |
| *A61F 2/10* | (2006.01) |
| *A61F 2/28* | (2006.01) |
| *A61F 2/30* | (2006.01) |
| *A61L 27/18* | (2006.01) |
| *A61L 27/58* | (2006.01) |

(52) U.S. Cl.
CPC .......... *A61F 2/30756* (2013.01); *A61L 27/18* (2013.01); *A61L 27/34* (2013.01); *A61L 27/58* (2013.01); *B32B 5/022* (2013.01); *D01D 5/0985* (2013.01); *A61F 2002/30062* (2013.01); *A61F 2210/0004* (2013.01); *A61L 2430/02* (2013.01); *B32B 2250/02* (2013.01); *B32B 2250/20* (2013.01)

(58) Field of Classification Search
CPC .... B32B 2250/20; D01D 5/08; D01D 5/0985; D02J 3/02; D04H 3/105
USPC .................. 264/103, 162, 171.1, 210.2, 555; 156/148, 167, 181; 28/107
See application file for complete search history.

(56) References Cited

U.S. PATENT DOCUMENTS

| | | | |
|---|---|---|---|
| 2011/0287082 A1* | 11/2011 | Smith | A61L 27/3813 424/444 |
| 2013/0110245 A1* | 5/2013 | Merklein | A61L 27/3817 623/17.16 |

FOREIGN PATENT DOCUMENTS

| | | | |
|---|---|---|---|
| JP | 2005177197 A * | 7/2005 | ............... B32B 5/24 |
| JP | 2011-056047 | 3/2011 | |
| JP | 2011-509786 | 3/2011 | |
| WO | 2009/093023 | 7/2009 | |
| WO | 2014/192803 | 12/2017 | |

* cited by examiner

Pore size = $\dfrac{4\gamma\cos\theta}{\Delta P}$

FIG.3

METHOD OF PRODUCING TISSUE REGENERATION SUBSTRATE

TECHNICAL FIELD

The present invention relates to a tissue regeneration substrate excellent in penetrability to cells as well as capable of effectively preventing cell leakage from the tissue regeneration substrate to accelerate tissue regeneration; and a method of producing the tissue regeneration substrate.

BACKGROUND ART

Recent advances in the cell engineering have enabled culturing of various animal cells, including human cells. Research on the reconstruction of human tissues or organs using such cells, that is, what we call regenerative medicine, has progressed rapidly. Specifically, research has been conducted on, for example, regenerative medicine for regeneration of tissues and organs such as cartilages, bones, skin, or blood vessels.

The point of regenerative medicine is whether cells can grow and differentiate to form a three-dimensional, living tissue-like structure. In an exemplary method, a substrate is implanted into the patient's body so that cells from the surrounding tissue or organ can penetrate into the substrate and grow and differentiate to regenerate tissue or an organ.

Endoscopic resection of foci in living tissue is often conducted using an automatic suturing device or the like. The resection of delicate tissue (e.g., the lung, bronchus, liver, or alimentary canal) or tissue weakened by lesions may cause tearing of the tissue if the resection wound is merely sutured. Surgery of the lung, for example, may cause air leakage. To avoid these risks, a suture reinforcing material is often sutured to the resection site of the living tissue.

Nonwoven fabrics made of bioabsorbable materials, such as that disclosed in Patent Literature 1, have been proposed as the substrates for regenerative medicine or the suture reinforcing materials. When a nonwoven fabric made of a bioabsorbable material is used as the substrate for regenerative medicine or the suture reinforcing material, the nonwoven fabric is expected to allow cells to penetrate and grow in the voids in the fabric, enabling rapid tissue regeneration. When such a nonwoven fabric is used as the reinforcing material for delicate tissue, it can prevent tearing of tissue and thus prevent air leakage or the like. The nonwoven fabrics also have the excellent feature that they eliminate the need for surgical removal because they are decomposed and absorbed in the living body after a certain period of time.

In actual, however, the nonwoven fabrics made of conventional bioabsorbable materials sometimes do not accelerate tissue regeneration as much as expected.

CITATION LIST

Patent Literature

Patent Literature 1: JP H05-076586 A

SUMMARY OF INVENTION

Technical Problem

It is known that, for ensured penetrability to cells, a suitable average pore size of the nonwoven fabric forming the tissue regeneration substrate is around 5 to 30 μm. As a result of intensive studies, the present inventors found out that while such conventional tissue regeneration substrates are excellent in penetrability to cells, some of the cells penetrating into the tissue regeneration substrate often pass through the substrate and leak out of the substrate. Since the cells penetrating into the tissue regeneration substrate leak out of the substrate, the concentration of cell components that actually remain in the affected area becomes insufficient. It is presumed that this leads to less accelerated tissue regeneration than expected. A smaller average pore size of the nonwoven fabric to prevent the cell leakage reduces the penetrability to cells, making it impossible to accelerate tissue regeneration.

In view of the situation in the art, an object of the present invention is to provide a tissue regeneration substrate excellent in penetrability to cells as well as capable of effectively preventing cell leakage from the tissue regeneration substrate to accelerate tissue regeneration; and a method of producing the tissue regeneration substrate.

Solution to Problem

The present invention provides a tissue regeneration substrate including: a nonwoven fabric made of a bioabsorbable material, the tissue regeneration substrate having a laminated structure in which a layer containing a nonwoven fabric having an average pore size of 20 to 50 μm and a layer containing a nonwoven fabric having an average pore size of 5 to 20 μm are integrated.

The present invention is described in more detail below.

As a result of intensive studies, the present inventors found out that the following tissue regeneration substrate can prevent the leakage of cells out of the tissue regeneration substrate and accelerate tissue regeneration without sacrificing excellent penetrability to cells: a tissue regeneration substrate having a laminated structure in which a layer containing a nonwoven fabric having an average pore size of 20 to 50 μm (hereinafter also referred to as "cell penetration layer") and a layer containing a nonwoven fabric having an average pore size of 5 to 20 μm (hereinafter also referred to as "cell leakage prevention layer") are integrated. The inventors thus completed the present invention.

It is important that not only the cell penetration layer but also the cell leakage prevention layer contains a nonwoven fabric having an average pore size within a certain range. The effect of preventing the leakage of floating cells in bodily fluids, blood, and the like alone can also be achieved by, for example, stacking a film made of a bioabsorbable material on the cell penetration layer. Such stacking of a film, however, cannot provide a sufficient tissue regeneration accelerating effect. The excellent effects of the present invention can be achieved only by using a nonwoven fabric having an average pore size of 5 to 20 μm as the cell leakage prevention layer.

The layer containing a nonwoven fabric having an average pore size of 5 to 20 μm almost completely blocks the passage of cells floating in bodily fluids, blood, and the like while allowing smooth passage of bodily fluids. The cell leakage prevention layer having this pore size accelerates penetration of attached cells from the cell penetration layer into the cell leakage prevention layer, as well as allowing sufficient supply of nourishment to the cells growing in the cell penetration layer. This is presumably the reason for the above excellent effects. Furthermore, since the cell leakage prevention layer can moderate stress caused by infiltration of bodily fluids, presumably the adhesiveness of the tissue regeneration substrate to an affected area is also maintained.

The cell penetration layer traps floating cells contained in bodily fluids, blood, and the like and serves as a scaffold for the growth of attached cells and cells penetrating from the surrounding tissue, thus accelerating tissue regeneration.

The cell penetration layer contains a nonwoven fabric made of a bioabsorbable material.

Examples of the bioabsorbable material forming the cell penetration layer include synthetic polymers such as polyglycolide, polylactide, poly-ε-caprolactone, lactide-glycolide copolymer, glycolide-ε-caprolactone copolymer, lactide-ε-caprolactone copolymer, polydioxanone, polycitric acid, polymalic acid, poly-α-cyanoacrylate, poly-β-hydroxy acid, polytrimethylene oxalate, polytetramethylene oxalate, polyorthoester, polyorthocarbonate, polyethylene carbonate, poly-γ-benzyl-L-glutamate, poly-γ-methyl-L-glutamate, and poly-L-alanine; polysaccharides such as starch, alginic acid, hyaluronic acid, chitin, pectinic acid, and derivatives thereof; and natural polymers such as proteins (e.g., gelatin, collagen, albumin, and fibrin). These bioabsorbable materials may be used alone or in combination of two or more thereof.

Preferred among the bioabsorbable materials is polyglycolide. The use of polyglycolide enables particularly excellent penetrability to cells and normal tissue regeneration. When polyglycolide in the form of fibers, for example, is immersed in saline at 37° C., it takes about 14 days for the tensile strength to decrease to half the pre-immersion value. Owing to such degradability, the substrate is gradually degraded and absorbed during the period where cells grow and regenerate tissue. The regenerated tissue is thus constructed even inside the substrate, which is considered to result in the construction of high-quality regenerated tissue. Furthermore, the substrate made of polyglycolide also has the advantage that it is less likely to cause tissue adhesion because inflammatory cells disappear within several days from implanting the substrate into the living body.

The "polyglycolide" as used herein means a polymer of glycolide, such as polyglycolic acid. Still, the polyglycolide may be a copolymer with other bioabsorbable component(s) such as lactide, ε-caprolactone, or p-dioxanone, as long as the effects of the present invention are not inhibited. Alternatively, the polyglycolide may be mixed with other bioabsorbable material(s) such as polylactide as long as the effects of the present invention are not inhibited.

When the polyglycolide is a copolymer with other bioabsorbable component(s) such as lactide, ε-caprolactone, or p-dioxanone, the lower limit of the amount of the glycolide component in the copolymer is preferably 60 mol %. When the amount of the glycolide components is 60 mol % or more, the excellent effects of the present invention, that is, excellent penetrability to cells and normal tissue regeneration, can be particularly exhibited.

When a mixture of the polyglycolide and other bioabsorbable material(s) such as polylactide is used, the lower limit of the amount of the polyglycolide in the mixture is preferably 50 mol %. When the amount of the polyglycolide is 50 mol % or more, the excellent effects of the present invention, that is, excellent penetrability to cells and normal tissue regeneration, can be particularly exhibited.

When the bioabsorbable material is polyglycolide, the lower limit of the weight average molecular weight of the polyglycolide is preferably 30000, and the upper limit thereof is preferably 400000. If the weight average molecular weight of the polyglycolide is less than 30000, the strength may be insufficient, and sufficient tissue reinforcing effect may not be obtained. If the weight average molecular weight is more than 400000, the tissue regeneration substrate degrades at a slower rate in the living body, which may cause foreign-body reaction. The lower limit of the weight average molecular weight of the polyglycolide is more preferably 50000. The upper limit thereof is more preferably 300000.

When the bioabsorbable material is polyglycolide, the melt flow rate may be used as an alternative index of the molecular weight of the polyglycolide. The lower limit of the melt flow rate of the polyglycolide is preferably 0.1 g/10 min, and the upper limit thereof is preferably 100 g/10 min. When the melt flow rate is within this range, the nonwoven fabric made of the polyglycolide is easily produced. The lower limit of the melt flow rate of the polyglycolide is more preferably 1 g/10. The upper limit thereof is more preferably 50 g/10 min.

The "melt flow rate" herein means the value measured at a load of 4 kgf after the polyglycolide is held and molten in a cylinder at 240° C. for 10 minutes.

The lower limit of the average pore size of the nonwoven fabric forming the cell penetration layer is 20 μm, and the upper limit thereof is 50 μm. When the cell penetration layer satisfies this average pore size, a tissue regeneration substrate excellent in penetrability to cells and suitable for normal tissue regeneration can be provided. Pores having a pore size of 20 to 50 μm in the nonwoven fabric are easy for cells to penetrate, and allow the cells to grow and differentiate in the cell penetration layer for tissue formation. If the average pore size is smaller than 20 μm, the floating cells contained in blood or the like cannot efficiently penetrate into the pores. If the average pore size is greater than 50 μm, although the floating cells can penetrate into the pores, the distance between the cells is too large. Cells adhering to the cell penetration layer or cells penetrating from the surrounding tissues thus cannot sufficiently grow and differentiate. The lower limit of the average pore size of the nonwoven fabric forming the cell penetration layer is preferably 22 μm, and the upper limit thereof is preferably 40 μm. The lower limit is more preferably 24 μm, and the upper limit thereof is more preferably 30 μm.

The "average pore size of the nonwoven fabric" as used herein means the average pore size measured by a bubble point method.

Measurement of the pore size distribution of the nonwoven fabric by the bubble point method is described below.

Figure 1:
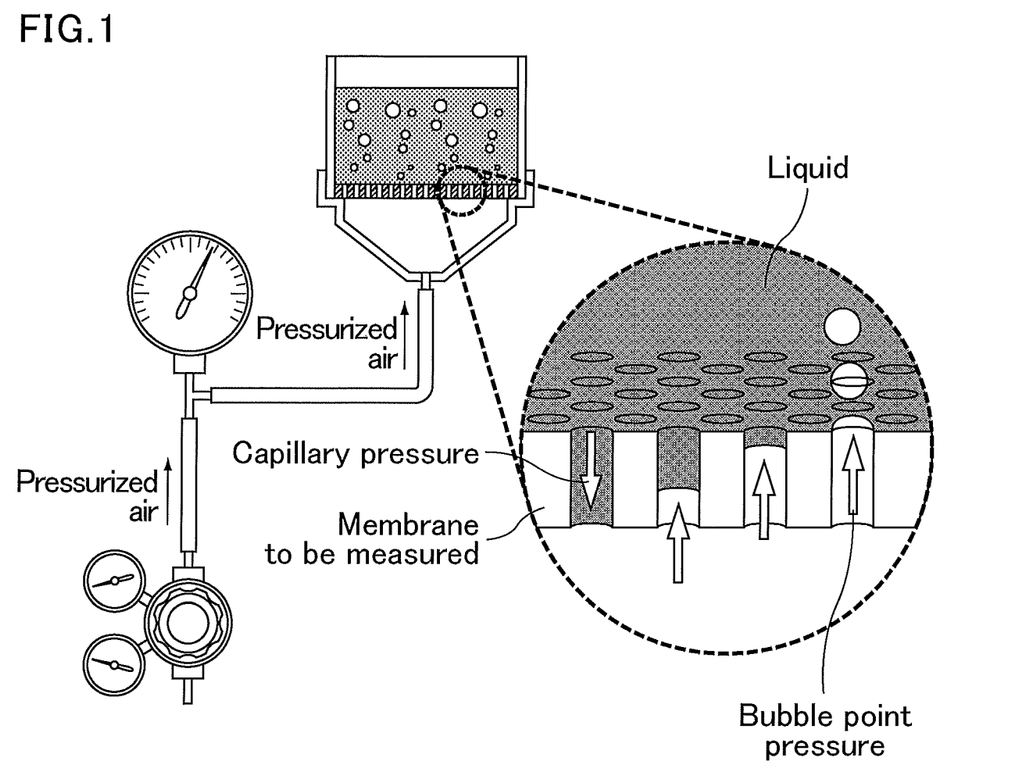
FIG. 1 is a schematic view illustrating a method for determining the pore size distribution of a nonwoven fabric by a bubble point method.

The bubble point method is a method in which, after a liquid that well wets the membrane to be measured is absorbed in the pores in the membrane, the membrane is placed in an instrument as shown in FIG. 1, then the air pressure is applied from the back side of the membrane to determine the minimum pressure (bubble point) at which bubble formation is observed on the membrane surface, and the pore distribution is estimated (FIG. 2) according to a relation between the surface tension of the liquid and the bubble point.

Specifically, a wetting liquid (e.g., a fluorine solvent, trade name: Porofil (registered trademark)) is absorbed into the nonwoven fabric to be measured, and then the membrane is placed in an instrument as shown in FIG. 1 (e.g., Porometer 3G produced by BEL Japan, Inc.) such that the specimen has a circular shape with a diameter of 25 mm. Then, the air pressure is applied from the back side of the nonwoven fabric to determine the minimum pressure (bubble point) at which formation of a bubble can be observed at the membrane surface.

Figure 2:
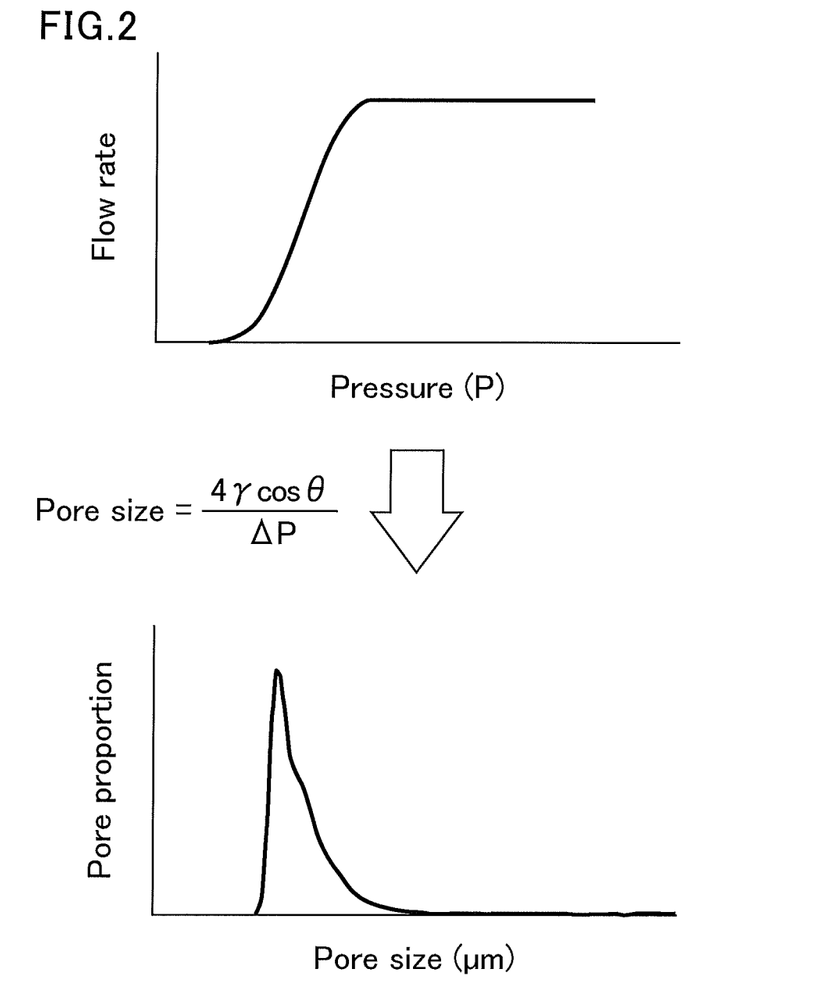
FIG. 2 is a schematic view illustrating a method for estimating the pore size distribution of a nonwoven fabric from data obtained by a bubble point method.

In the formula for calculating the pore size shown in in FIG. 2, $\gamma$ represents the surface tension of the wetting liquid;

θ represents the contact angle of the wetting liquid on the nonwoven fabric material; and ΔP represents the bubble point pressure.

The nonwoven fabric forming the cell penetration layer may have any average fiber diameter. The lower limit thereof is preferably 10 μm, and the upper limit thereof is preferably 50 μm. When the average fiber diameter of the nonwoven fabric is within this range, the average pore size is easily adjusted to the range specified above. The lower limit of the average fiber diameter of the nonwoven fabric is more preferably 15 μm, and the upper limit thereof is more preferably 40 μm.

The average fiber diameter of the nonwoven fabric can be obtained by measuring, on a scanning electron microscopic image of the nonwoven fabric taken at 1000-fold magnification, the diameter at the midpoint of all the fibers whose fiber diameter is measurable, and calculating the average of the measured diameters.

The cell penetration layer may have any thickness. The lower limit thereof is preferably 300 μm, and the upper limit thereof is preferably 2.0 mm. If the thickness of the cell penetration layer is smaller than 300 μm, the strength may be insufficient and the tissue regeneration substrate may not be usable for reinforcement of delicate tissue. If the thickness is greater than 2.0 mm, the handleability is poor. The lower limit of the thickness of the cell penetration layer is more preferably 450 μm and the upper limit thereof is more preferably 1.5 mm.

The cell leakage prevention layer prevents the leakage of floating cells in bodily fluids, blood, and the like out of the tissue regeneration substrate while allowing smooth passage of bodily fluids. The cell leakage prevention layer thus serves to accelerate the penetration of cells into the cell penetration layer and ensure the supply of nourishment to the cells growing in the cell penetration layer. In addition, the cells grown in the cell penetration layer can also penetrate inside the cell leakage prevention layer, which can prevent falling of the cell leakage prevention layer alone.

The cell leakage prevention layer contains a nonwoven fabric made of a bioabsorbable material.

The bioabsorbable material forming the cell leakage prevention layer may be the same as that used for the cell penetration layer. The bioabsorbable material forming the cell leakage prevention layer may be the same as or different from that forming the cell penetration layer.

The lower limit of the average pore size of the nonwoven fabric forming the cell leakage prevention layer is 5 μm, and the upper limit thereof is 20 μm. When the cell leakage prevention layer satisfies this average pore size, the layer can prevent the leakage of floating cells in bodily fluids, blood, and the like out of the tissue regeneration substrate while allowing smooth passage of bodily fluids, accelerate the penetration of cells into the cell penetration layer, and ensure the supply of nourishment to the cells growing in the cell penetration layer. Furthermore, the cells grown in the cell penetration layer can also penetrate inside the cell leakage prevention layer, which can prevent falling of the cell leakage prevention layer alone. If the average pore size of the nonwoven fabric forming the cell leakage prevention layer is greater than 20 μm, the cell leakage from the tissue regeneration substrate cannot be sufficiently prevented. If the average pore size of the nonwoven fabric forming the cell leakage prevention layer is smaller than 5 μm, the cell penetration into the cell penetration layer may be reduced or nourishment may be insufficiently supplied to the cells in the cell penetration layer, which may lead to insufficient acceleration of tissue regeneration. The lower limit of the average pore size of the nonwoven fabric forming the cell leakage prevention layer is preferably 6 μm, and the upper limit thereof is preferably 18 μm. The lower limit is more preferably 7 μm, and the upper limit is more preferably 16 μm.

The nonwoven fabric forming the cell leakage prevention layer may have any average fiber diameter. The lower limit thereof is preferably 0.7 μm and the upper limit thereof is preferably 7.0 μm. When the average fiber diameter of the nonwoven fabric is within this range, the average pore size is easily adjusted to the range specified above. The lower limit of the average fiber diameter of the nonwoven fabric is more preferably 0.9 μm, and the upper limit thereof is more preferably 5.0 μm.

The cell leakage prevention layer may have any thickness. The lower limit thereof is preferably 10 μm, and the upper limit thereof is preferably 150 μm. If the thickness of the cell leakage prevention layer is smaller than 10 μm, the cell leakage from the tissue regeneration substrate may not be sufficiently prevented. If the thickness is greater than 150 μm, the cell penetration into the cell penetration layer may be reduced or nourishment may be insufficiently supplied to the cells in the cell penetration layer, which may lead to insufficient acceleration of tissue regeneration. The lower limit of the thickness of the cell leakage prevention layer is more preferably 30 μm, and the upper limit thereof is more preferably 100 μm.

The tissue regeneration substrate of the present invention may have a laminated structure in which two layers, the cell penetration layer and the cell leakage prevention layer, are integrated, or may have a laminated structure in which three layers, the cell penetration layer, the cell leakage prevention layer, and the cell penetration layer, are integrated in the given order.

In particular, the tissue regeneration substrate with the three-layer laminated structure accelerates tissue regeneration at a very high efficiency because when such a tissue regeneration substrate is implanted, cells can penetrate from its both sides while the cells penetrating into the substrate do not leak out of the tissue regeneration substrate because of the cell leakage prevention layer in the middle.

When the tissue regeneration substrate of the present invention has a laminated structure in which two layers, the cell penetration layer and the cell leakage prevention layer, are integrated, a layer in which fibers having an average fiber diameter of 0.1 to 0.7 μm are aggregated (hereinafter, also referred to as "microfiber aggregate layer") may be stacked on the surface of the cell leakage prevention layer remote from the cell penetration layer. Stacking such a microfiber aggregate layer can further prevent the cell leakage from the tissue regeneration substrate.

The bioabsorbable material forming the microfiber aggregate layer may be the same as that used for the cell penetration layer or the cell leakage prevention layer. The bioabsorbable material forming the microfiber aggregate layer may be the same as or different from that forming the cell penetration layer or the cell leakage prevention layer.

The lower limit of the average fiber diameter of the fibers forming the microfiber aggregate layer is preferably 0.2 μm, and the upper limit thereof is preferably 0.65 μm. When the average fiber diameter of the fibers of the microfiber aggregate layer is within this range, the cell leakage from the tissue regeneration substrate can be further prevented without affecting the cell penetration into the cell penetration layer or the supply of nourishment to the cells in the cell penetration layer. The lower limit of the average fiber diameter of the fibers of the microfiber aggregate layer is more preferably 0.3 μm, and the upper limit thereof is more preferably 0.6 μm.

The microfiber aggregate layer may have any thickness. The lower limit thereof is preferably 1.0 μm, and the upper limit thereof is preferably 100 μm. If the thickness of the microfiber aggregate layer is smaller than 1.0 μm, the effect of preventing the cell leakage from the tissue regeneration substrate may not be obtained. If the thickness is greater than 100 μm, the cell penetration into the cell penetration layer may be low and the nourishment may be insufficiently supplied to the cells in the cell penetration layer, which may lead to insufficient acceleration of tissue regeneration. The lower limit of the thickness of the microfiber aggregate layer is more preferably 1.5 μm, and the upper limit thereof is more preferably 80 μm.

In the tissue regeneration substrate of the present invention, the cell penetration layer and the cell leakage prevention layer are integrated.

If the cell penetration layer and the cell leakage prevention layer are not integrated, the cell penetration layer and the cell leakage prevention layer may partially or entirely separate from each other when cells are seeded on the tissue regeneration substrate of the present invention or when the substrate is implanted in tissue or an organ. If the cell penetration layer and the cell leakage prevention layer even partially separate from each other, cells may collect in the space formed at the separation site and thus fail to regenerate a normal tissue or organ.

As used herein, the phrase "the cell penetration layer and the cell leakage prevention layer are integrated" means that the cell penetration layer and the cell leakage prevention layer do not separate from each other even if the tissue regeneration substrate of the present invention is folded when implanted in tissue or an organ. Quantitatively, the delamination strength as measured in accordance with Determination of delamination strength specified in JIS L 1021-9 is preferably 0.1 N or more, more preferably 0.3 N or more.

Possible methods for integrating the cell penetration layer and the cell leakage prevention layer include bonding with a medical adhesive and bonding after dissolving part of the surface of the cell penetration layer or the cell leakage prevention layer with a solvent. Unfortunately, bonding the cell penetration layer and the cell leakage prevention layer by these methods may cause clogging of the pores of each layer at the bonding face. Such clogged pores may prevent smooth passage of bodily fluids and inhibit the supply of nourishment to the cells in the cell penetration layer.

After intensive studies, the present inventors found out that the following method enables the integration of the cell penetration layer and the cell leakage prevention layer without clogging the pores at the bonding face: a method of producing the tissue regeneration substrate, including the steps of: preparing the cell penetration layer; discharging threads made of a bioabsorbable material onto the cell penetration layer by melt blowing to form the cell leakage prevention layer to produce a stack; needle-punching the stack to integrate the cell penetration layer and the cell leakage prevention layer. Such a method of producing the tissue regeneration substrate is also included in the present invention (hereinafter, this method is also referred to as "first method of producing the tissue regeneration substrate of the present invention")

After intensive studies, the present inventors also found out that the following method enables the integration of the cell penetration layer and the cell leakage prevention layer without clogging the pores at the bonding face: a method of producing the tissue regeneration substrate, including the steps of: preparing the cell penetration layer; preparing the cell leakage prevention layer; stacking the cell penetration layer and the cell leakage prevention layer to produce a stack; and needle-punching the stack to integrate the cell penetration layer and the cell leakage prevention layer. Such a method of producing the tissue regeneration substrate is also included in the present invention (hereinafter, this method is also referred to as "second method of producing the tissue regeneration substrate of the present invention")

In the following, the methods of producing the tissue regeneration substrate of the present invention are described in detail (hereinafter, in the description of matters common to the first and second methods of producing the tissue regeneration substrate of the present invention, these methods may also referred to simply as "the method of producing the tissue regeneration substrate of the present invention").

In the method of producing the tissue regeneration substrate of the present invention, first, the step of preparing the cell penetration layer is performed.

The cell penetration layer may be prepared by any method. For example, the cell penetration layer may be produced by a conventionally known method, such as electrospinning deposition, melt blowing, needle punching, spun bonding, flash spinning, hydroentangling, air laying, thermal bonding, resin bonding, or wet processing. In particular, needle punching is suitable for the preparation of the cell penetration layer.

The method of producing the tissue regeneration substrate of the present invention preferably includes, after the step of preparing the cell penetration layer, the step of fluffing a surface of the cell penetration layer on which the cell leakage prevention layer is to be stacked. Fluffing the surface of the cell penetration layer in advance further improves the adhesion of the cell penetration layer to the cell leakage prevention layer.

Specifically fluffing may be performed by napping, with a napping machine, the surface of the cell penetration layer on which the cell leakage prevention layer is to be stacked, for example. In cases where the cell penetration layer is produced by needle punching, the surface of the resulting cell penetration layer is already napped, so that the same effects as in the case of performing fluffing can be obtained.

In the first method of producing the tissue regeneration substrate of the present invention, next, the step is performed of discharging threads made of a bioabsorbable material on the cell penetration layer by melt blowing to form the cell leakage prevention layer to produce a stack.

The melt blowing is a melt spinning process in which a bioabsorbable material as a raw material is formed into a nonwoven fabric in one step. Specifically, a bioabsorbable material molten in an extruder is blown by high-temperature, high-velocity air flows in a thread form from a die having multiple spinnerets in its width direction toward fiber trapping points. The resin stretched into fibers is accumulated on the conveyer. The fibers are entangled and fused with one another between the discharge and the accumulation, thereby producing a nonwoven fabric. In the first method of producing the tissue regeneration substrate of the present invention, the cell penetration layer is placed on the conveyer at a position in front of the fiber trapping points for melt blowing. While transferring the cell penetration layer with the conveyer, the fibers are discharged onto the cell penetration layer to form the cell leakage preventions layer.

The properties such as the fiber diameter, the density, and the thickness of the cell penetration layer to be formed can be controlled by adjusting such factors as the polymer discharge rate, the air velocity around the outlets, or the speed of the conveyer in melt blowing.

In the second method of producing the tissue regeneration substrate of the present invention, the step of preparing the cell leakage prevention layer separately from the cell penetration layer is performed, and the step of stacking the obtained cell penetration layer and cell leakage prevention layer to produce a stack is performed.

The cell leakage prevention layer may be prepared by any method. For example, the layer can be produced by discharging threads made of a bioabsorbable material by melt blowing.

The stack can be obtained by stacking the cell penetration layer and the cell leakage prevention layer on top of each other.

In the method of producing the tissue regeneration substrate of the present invention, subsequently, the step of needle-punching the stack to integrate the cell penetration layer and the cell leakage prevention layer is performed.

Needle punching can reliably integrate the cell penetration layer and the cell leakage prevention layer without clogging the pores in each layer at the bonding surface.

The direction of the entry of the needles in needle-punching of the stack is not limited.

In the method of producing the tissue regeneration substrate of the present invention, subsequently, the stack may be heat-set. When the stack is heat-set, the resulting tissue regeneration substrate can have a smooth surface, which is expected to improve the handleability.

The stack can be heat-set by, for example, roll pressing at a temperature higher than the crystallization point of the polymer forming the stack.

When the tissue regeneration substrate of the present invention includes the microfiber aggregate layer, for example, the microfiber aggregate layer is formed by discharging microfibers onto the cell leakage prevention layer by electro-spinning deposition, whereby a stack is formed. Then, the step of needle-punching the stack to integrate the cell penetration layer, the cell leakage prevention layer, and the microfiber aggregate layer is performed.

The tissue regeneration substrate of the present invention has the laminated structure in which the cell penetration layer and the cell leakage prevention layer are integrated. When implanted as a scaffold to reinforce tissue or accelerate tissue regeneration, therefore, the tissue regeneration substrate exhibits excellent cell-trapping properties and excellent penetrability to cells, and also can prevent cell leakage from the tissue regeneration substrate. The cell density in the tissue regeneration substrate thus can be increased, accelerating rapid regeneration of tissue. Specifically, the tissue regeneration substrate is suitable as a substrate for regenerative medicine for regenerating tissues and organs such as cartilages, bones, skin, or blood vessels.

These tissues or organs may be regenerated by, for example, implanting the tissue regeneration substrate of the present invention in a site of the tissue or organ to be regenerated. Here, cells may be seeded on the tissue regeneration substrate of the present invention in advance.

When the tissue regeneration substrate of the present invention is applied to a site where rapid healing is desired, such as pulmonary fistula, bronchial stumps, pancreatic fistula, or biliary fistula, the substrate is useful as a scaffold to reinforce delicate tissue or accelerate tissue regeneration. The effects are remarkable especially when the substrate is applied to sites where tissue is less likely to move, such as bronchial stumps, pancreatic fistula, or biliary fistula.

The tissue regeneration substrate of the present invention is applied postoperatively to delicate tissue such that it covers the tissue. When an automatic suturing device is used, the tissue regeneration substrate of the present invention is also useful in that applying the tissue regeneration substrate of the present invention to tissue before suturing using an automatic suturing device can prevent air leakage from the lung or bodily fluid leakage from various tissues.

Advantageous Effects of Invention

The present invention provides a tissue regeneration substrate excellent in penetrability to cells as well as capable of effectively preventing cell leakage from the tissue regeneration substrate to accelerate tissue regeneration; and a method of producing the tissue regeneration substrate.

DESCRIPTION OF EMBODIMENTS

The embodiments of the present invention are described in more detail below with reference to examples. The present invention, however, should not be limited to the example.

Example 1

(1) Preparation of Cell Penetration Layer

Polyglycolide having a weight average molecular weight of 250000 was used as a bioabsorbable material. A fabric made of yarn spun from the polyglycolide was needle-punched to form a nonwoven fabric. In this manner, a cell penetration layer having an average fiber diameter of about 16 μm and a thickness of about 1.5 mm was obtained.

A fluorine-containing solvent (trade name: Porofil (registered trade mark)) as a wetting agent was absorbed into the obtained cell penetration layer. The layer was then placed on Porometer 3G produced by BEL Japan, Inc. such that the specimen had a circular shape with a diameter of 25 mm. Then, the air pressure was applied from the back side of the cell penetration layer to determine the minimum pressure (bubble point) at which formation of a bubble was observed at the membrane surface. A graph of the pore size distribution of the cell penetration layer was obtained based on the bubble point. The average pore size calculated from the graph was 28 μm.

(2) Stacking of Cell Leakage Prevention Layer

The obtained cell penetration layer was placed on the conveyer at a position in front of the fiber trapping points for melt blowing. While moving the conveyer, threads made of polyglycolide were discharged onto the cell penetration layer by melt blowing, thus a cell leakage prevention layer was stacked on the cell penetration layer.

The melt blowing was performed using polyglycolide having a weight average molecular weight of 250000 as a raw material at a polymer discharge rate of 0.2 kg/h and an air velocity around the outlets of 11 m/sec. The speed of the conveyor was set such that the cell leakage prevention layer obtained by the melt blowing had a density of 10 g/m².

Separately, a cell leakage prevention layer alone was produced under the same conditions. The average pore size of this cell leakage prevention layer was 12 μm as calculated by the bubble point method.

(3) Integration of Cell Penetration Layer and Cell Leakage Prevention Layer

The obtained stack was needle-punched such that the needles entered from the cell leakage prevention layer-side of the stack, whereby the cell penetration layer and the cell leakage prevention layer were integrated.

Example 2

A tissue regeneration substrate was obtained in the same manner as in Example 1 except that in the preparation of the cell penetration layer the cell penetration layer obtained by needle punching was hot-pressed to achieve a smooth surface.

Example 3

A tissue regeneration substrate was obtained in the same manner as in Example 1 except that in the preparation of the cell penetration layer the cell penetration layer obtained by needle punching was hot-pressed to achieve a smooth surface and then fluffed by brushing with a brass brush, and that the cell leakage prevention layer was stacked on the fluffed side.

Example 4

(1) Preparation of Cell Penetration Layer

Polyglycolide having a weight average molecular weight of 250000 was used as a bioabsorbable material. A fabric made of yarn spun from the polyglycolide was needle-punched to form a nonwoven fabric. In this manner, two cell penetration layers were obtained: one having an average fiber diameter of about 16 μm and a thickness of about 1.5 mm, and the other having an average fiber diameter of about 16 μm and a thickness of about 0.5 mm.

Each obtained cell penetration layer had average pore size of 28 μm as calculated by the bubble point method.

(2) Preparation of Cell Leakage Prevention Layer

A cell leakage prevention layer having average fiber diameter of about 2 μm and a thickness of about 50 μm was obtained by melt blowing using polyglycolide having a weight average molecular weight of 250000 as a bioabsorbable material. The cell leakage prevention layer had an average pore size of 12 μm as calculated by the bubble point method.

(3) Integration of Cell Penetration Layer and Cell Leakage Prevention Layer

The cell penetration layer having a thickness of about 1.5 mm, the cell leakage prevention layer having a thickness of about 50 μm, and the cell penetration layer having a thickness of about 0.5 mm were stacked in the given order to produce a three-layer stack.

The three-layer stack was needle-punched from the side of the cell penetration layer having a thickness of about 0.5 mm to integrate the three layers. Thus, a tissue regeneration substrate was obtained.

Comparative Example 1

Polyglycolide having a weight average molecular weight of 250000 was used as a bioabsorbable material. A fabric made of yarn spun from the polyglycolide was needle-punched to form a nonwoven fabric having an average fiber diameter of about 16 μm and a thickness of about 1.5 mm. This nonwoven fabric was used as a tissue regeneration substrate. The obtained nonwoven fabric had an average pore size of 28 μm as determined by the bubble point method.

Comparative Example 2

A nonwoven fabric having an average fiber diameter of about 2 μm and a thickness of about 50 μm was obtained by melt blowing using polyglycolide having a weight average molecular weight of 250000 as a bioabsorbable material. This nonwoven fabric was used as a tissue regeneration substrate. The obtained nonwoven fabric had an average pore size of 12 μm as determined by the bubble point method.

Comparative Example 3

A tissue regeneration substrate was obtained in the same manner as in Example 1 except that the integration treatment by needle punching was not performed.

Comparative Example 4

A tissue regeneration substrate was obtained in the same manner as in Example 2 except that the integration treatment by needle punching was not performed.

Comparative Example 5

A tissue regeneration substrate was obtained in the same manner as in Example 3 except that the integration treatment by needle punching was not performed.

Evaluation

The tissue regeneration substrates obtained in the examples and the comparative examples were evaluated by the following methods.

Table 1 shows the results.

(1) Evaluation of Particle Trapping Rate

Polystyrene particles having an average particle size of 20 μm were dispersed into an aqueous solution of ethanol (water/ethanol (volume ratio)=80/20) to prepare a particle dispersion.

The tissue regeneration substrate was cut into a square shape (20 mm×20 mm) and fixed onto metal mesh.

The particle dispersion (2 mL) was slowly added dropwise from the cell penetration layer-side (in Example 4, the about 1.5 mm-thick cell penetration layer-side) of the tissue regeneration substrate, so that the dispersion permeated the tissue regeneration substrate. The absorbance of the particle dispersion at a wavelength of 230 nm was measured before and after the permeation, and the particle concentration (pcs/mL) was calculated based on a calibration curve obtained by measuring the absorbance of a polystyrene latex particle dispersion of a known.

concentration. The number of particles in the particle dispersion before and after the permeation was determined from the obtained particle concentration before and after the permeation and the volume of the dispersion calculated from the weight of the dispersion before and after the permeation. The particle trapping rate (%) was calculated by the following formula.

Figure 3:
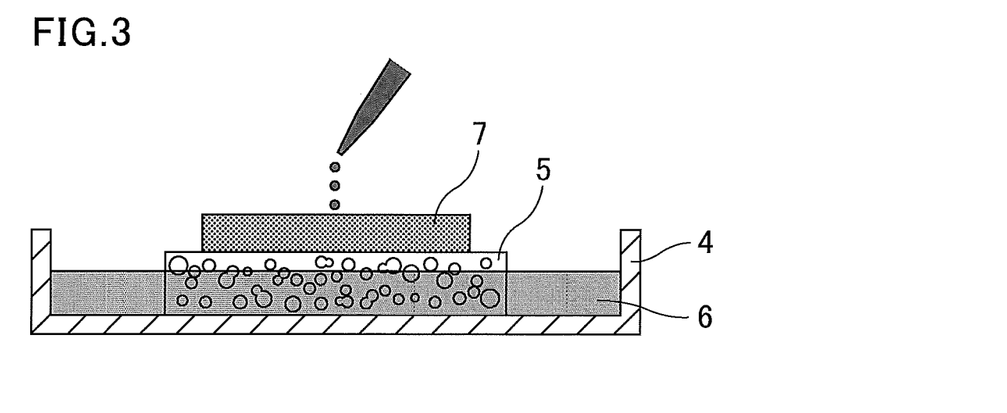
FIG. 3 is a schematic view illustrating an evaluation method used in examples and comparative examples.

Particle trapping rate (%)=(Number of particles in particle dispersion before permeation−Number of particles in particle dispersion after permeation)/Number of particles in particle dispersion before permeation (2) Evaluation of Cell Retention Cells were seeded on the tissue regeneration substrates in accordance with the culturing method illustrated in FIG. 3. The growth of the cells was evaluated.

Specifically, a sponge body 5 was placed on a petri dish 4. A culture medium 6 was poured into the petri dish such that the surface of the sponge body 5 was impregnated with the medium (the culture medium was thus supplied only from the sponge body 5). The tissue regeneration substrates 7 produced in the examples and the comparative examples were each placed on the corresponding sponge body 5. In the examples and Comparative Examples 3 to 5, the tissue regeneration substrate was placed with the cell leakage prevention layer downward so that it contacted the sponge body 5. In Example 4, the tissue regeneration substrate was placed with the cell penetration layer having a thickness of about 0.5 mm downward such that it contacted the sponge body 5.

On the tissue regeneration substrate 7 arranged in this manner, fibroblasts were seeded to achieve a seed density of $1\times10^5$ pcs/cm$^2$. The fibroblasts were then cultured for seven days. The culture medium 6 was changed every day. After the seven-day culture, the number of cells contained in the tissue regeneration substrate 7 was counted by MTT assay. The number of cells in the tissue regeneration substrates of the examples and comparative examples was expressed relative to the number of cells in the tissue regeneration substrate of Comparative Example 1 taken as 100. Table 1 shows the results.

(3) Evaluation of Integrity (Qualitative Evaluation)

The integrity of the cell regeneration substrate was evaluated according to the following criteria.

oo (Excellent): Folding the tissue regeneration substrate did not cause separation of the cell penetration layer and the cell leakage prevention layer from each other, and an attempt to manually separate the cell penetration layer and the cell leakage prevention layer from each other caused breaking of the cell penetration layer or the cell leakage prevention layer before separation.

o (Good): Folding the tissue regeneration substrate did not cause separation of the cell penetration layer and the cell leakage prevention layer from each other, and the cell penetration layer and the cell leakage prevention layer were not easily manually separated from each other.

Δ (acceptable): Folding the tissue regeneration substrate caused partial separation of the cell penetration layer and the cell leakage prevention layer from each other, and the cell penetration layer and the cell leakage prevention layer were easily manually separated from each other.

x (Poor): Folding the tissue regeneration substrate caused the entire separation of the cell penetration layer and the cell leakage prevention layer from each other, and the cell penetration layer and the cell leakage prevention layer were easily manually separated from each other.

(4) Evaluation of Integrity (Quantitative Evaluation)

The integrity of the cell regeneration substrate was evaluated by measuring the delamination strength in accordance with Determination of delamination strength specified in JIS L 1021-90.

Specifically, the obtained tissue regeneration substrate was cut into a strip of 20 mm wide×50 mm long, and the cell penetration layer and the cell leakage prevention layer were manually separated from each other by 25 mm in the length direction in advance to form grip portions. The strip was used as a sample. The grip portion of each layer of the obtained sample was held with chucks (gripping distance 20 mm) and pulled with an autograph ("AGS-J" produced by SHIMADZU Corporation, load cell 50 N) at a pulling speed of 100 mm/min to determine the delamination strength. JIS L 1021-9 specifies that the sample size is 50 mm wide×200 mm long, and the length of the portions to be separated in advance (length of the grip portions) is 50 mm. Yet, in view of the fact that the cell regeneration substrate is for implantation in tissue or an organ, the sample was prepared as described above. JIS L 1021-9 also specifies that the sample should be allowed to stand in a constant temperature and humidity chamber (20° C., 65%) for 24 hours. Yet, since the sample is a substrate made of a degradable polymer, this procedure was omitted and the measurement was performed immediately after the preparation of the sample.

For the cell regeneration substrate of Example 4, the sample was prepared by separating the layers of the 20 mm×50 mm strip from each other by 25 mm in the vertical direction, and the cell penetration layer having a thickness of about 1.5 mm and the cell leakage prevention layer having a thickness of about 50 μm were held with chucks. The delamination strength between these two layers was measured by the tensile test under the above conditions.

TABLE 1

| | Evaluation of particle trapping rate (%) | Evaluation of cell retention (number of cells) | Evaluation of integrity | |
|---|---|---|---|---|
| | | | Qualitative evaluation | Delamination strength (N) |
| Exmaple 1 | 0.922 | 141 | oo | 0.42 |
| Exmaple 2 | 0.818 | 128 | o | 0.33 |
| Exmaple 3 | 0.932 | 135 | oo | 0.36 |
| Exmaple 4 | 0.947 | 145 | oo | Not evaluated (cell leakage prevention layer broke during delamination test) |
| Comparative Exmaple 1 | 0.840 | 100 | — | — |
| Comparative Exmaple 2 | 0.983 | 54 | — | — |
| Comparative Exmaple 3 | 0.962 | 138 | Δ | 0.02 |
| Comparative Exmaple 4 | 0.955 | 129 | x | 0.02 |
| Comparative Exmaple 5 | 0.971 | 130 | Δ | 0.06 |

INDUSTRIAL APPLICABILITY

The present invention provides a tissue regeneration substrate excellent in penetrability to cells as well as capable of effectively preventing cell leakage from the tissue regeneration substrate to accelerate tissue regeneration; and a method of producing the tissue regeneration substrate.

REFERENCE SIGNS LIST 4 petri dish
5 sponge body
6 culture medium
7 tissue regeneration substrate

The invention claimed is:

1. A method of producing a tissue regeneration substrate comprising:
   preparing a layer containing a nonwoven fabric having an average pore size of 20 to 50 μm;
   discharging threads made of a bioabsorbable material on the layer containing a nonwoven fabric having an average pore size of 20 to 50 μm by melt blowing to form a layer containing a nonwoven fabric having an average pore size of 5 to 18 μm to produce a stack; and
   needle-punching the stack to integrate the layer containing a nonwoven fabric having an average pore size of 20 to 50 μm and the layer containing a nonwoven fabric having an average pore size of 5 to 18 μm.

2. A method of producing a tissue regeneration substrate comprising:
   preparing a layer containing a nonwoven fabric having an average pore size of 20 to 50 μm;
   preparing a layer containing a nonwoven fabric having an average pore size of 5 to 18 μm;
   stacking the layer containing a nonwoven fabric having an average pore size of 20 to 50 μm and the layer containing a nonwoven fabric having an average pore size of 5 to 18 μm to produce a stack; and
   needle-punching the stack to integrate the layer containing a nonwoven fabric having an average pore size of 20 to 50 μm and the layer containing a nonwoven fabric having an average pore size of 5 to 18 μm.

3. The method of producing the tissue regeneration substrate according to claim 1, further comprising, after preparing the layer containing a nonwoven fabric having an average pore size of 20 to 50 μm, fluffing a surface of the layer containing a nonwoven fabric having an average pore size of 20 to 50 μm on which the layer containing a nonwoven fabric having an average pore size of 5 to 18 μm is to be stacked.

4. The method of producing the tissue regeneration substrate according to claim 2, further comprising, after preparing the layer containing a nonwoven fabric having an average pore size of 20 to 50 μm, fluffing a surface of the layer containing a nonwoven fabric having an average pore size of 20 to 50 μm on which the layer containing a nonwoven fabric having an average pore size of 5 to 18 μm is to be stacked.

* * * * *